(12) United States Patent
Fontenot

(10) Patent No.: US 11,849,992 B1
(45) Date of Patent: Dec. 26, 2023

(54) INCREASING PLASMA GENERATED SPECIES (PGS) IN NON-THERMAL PLASMA (NTP) MEDICAL TREATMENT

(71) Applicant: Mark G. Fontenot, Lafayette, LA (US)

(72) Inventor: Mark G. Fontenot, Lafayette, LA (US)

( * ) Notice: Subject to any disclaimer, the term of this patent is extended or adjusted under 35 U.S.C. 154(b) by 327 days.

(21) Appl. No.: 17/149,515

(22) Filed: Jan. 14, 2021

(51) Int. Cl.
| | | |
|---|---|---|
| *A61B 18/04* | (2006.01) |
| *A61B 18/14* | (2006.01) |
| *A61B 18/00* | (2006.01) |
| *A61B 18/06* | (2006.01) |

(52) U.S. Cl.
CPC ........... *A61B 18/042* (2013.01); *A61B 18/14* (2013.01); *A61B 2018/00583* (2013.01); *A61B 2018/048* (2013.01); *A61B 2018/062* (2013.01); *A61B 2018/147* (2013.01)

(58) Field of Classification Search
CPC .......... A61B 18/042; A61B 18/14; A61B 2018/00583; A61B 2018/048; A61B 2018/062; A61B 2018/147; H05H 1/2406
See application file for complete search history.

(56) References Cited

U.S. PATENT DOCUMENTS

| | | | | |
|---|---|---|---|---|
| 3,838,242 A | * | 9/1974 | Goucher | A61B 18/042 219/121.36 |
| 8,521,274 B2 | * | 8/2013 | Gutsol | A61B 18/042 607/2 |
| 11,229,806 B2 | * | 1/2022 | Barbarat | H05H 1/2406 |
| 2022/0151698 A1 | * | 5/2022 | Winkelman | A61B 18/14 |

* cited by examiner

*Primary Examiner* — Michael F Peffley
(74) *Attorney, Agent, or Firm* — BAKER DONELSON PC

(57) ABSTRACT

Embodiments include a system comprising a non-thermal plasma (NTP) device and at least one container including supersaturated gas emulsion (SSGE). A method is described involving configuring a supersaturated gas emulsion (SSGE) for application to a treatment site and configuring a device to generate a non-thermal plasma (NTP) at the treatment site.

20 Claims, 19 Drawing Sheets

| COMPONENT | %W/W |
|---|---|
| WATER (AQUA) | 32.900% |
| PERFLUORODECALIN | 30.000% |
| GLYCERIN | 20.400% |
| PHOSPHOLIPON 90H | 10.200% |
| POLAWAX | 3.000% |
| TOCOPHERYL ACETATE | 0.500% |
| SYMDIOL 68 | 1.000% |
| HYDROLITE - 5 | 2.000% |
| TOTAL | 100.000% |
| Symdiol 68: INCI Name: 1,2-Hexanediol (and) Caprylyl Glycol | |
| Hydrolite 5 INCI Name: Pentylene Glycol | |

Figure 4

- 817 Torr (mm Hg) peak SSOE oxygen measured using a fiberoptic oxygen sensor.
  - 5 times greater than atmospheric oxygen (160 mm Hg).
- After nearly two hours of fiberoptic oxygen measurement, SSOE oxygen outgassing continued at a level of 567 Torr (mm Hg).
  - Nearly 4 times the amount of oxygen compared to atmospheric oxygen after 2 hours.

INCREASING PLASMA GENERATED SPECIES (PGS) IN NON-THERMAL PLASMA (NTP) MEDICAL TREATMENT

RELATED APPLICATION

This application claims the benefit of United States (U.S.) Patent Application No. 62/961,559, filed Jan. 15, 2020.

TECHNICAL FIELD

The present invention relates generally to systems and methods including the generation and application of non-thermal plasma.

BACKGROUND

There is a need for systems and methods involving dielectric barrier discharge (DBD)-based non-thermal plasma (NTP) technology to cure disease, improve quality of life, and extend lives of patients.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE FIGURES

FIG. 4 shows a table including the component ingredients in an example embodiment of the SSGE, including water, perfluorodecalin, glycerin, phospholipids, Polawax, Vitamin E, and preservative, under an embodiment.

DETAILED DESCRIPTION

Non-Thermal (Cold) Plasma Used in Medicine

Figure 1:
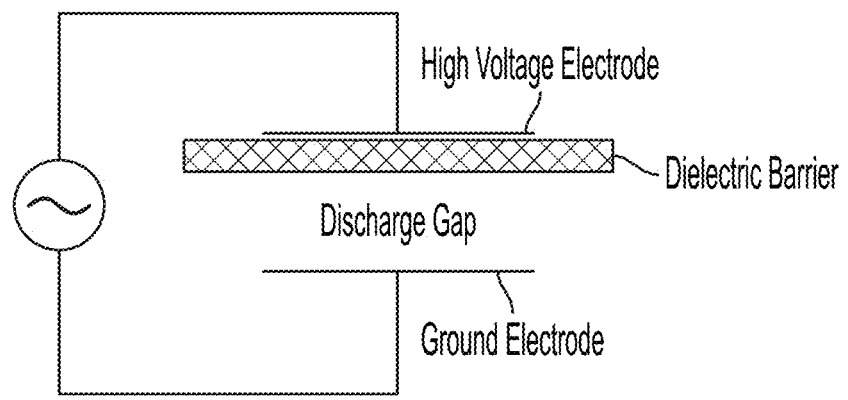
FIG. 1 is a block diagram of a DBD device configuration, under an embodiment.

The development of devices to produce cold plasma under conditions of atmospheric pressure form the fundamental basis for the emergence of plasma-related application areas in medicine, and the medical literature describes the many clinical benefits of applications of non-thermal plasma in medicine. Cold plasma, also referred to as non-thermal plasma (NTP), comprises a myriad of active components such as charged particles, electric current, ultraviolet (UV) radiation, and reactive gas species which can function independently or synergistically. The combination of the different constituent ions and reactive species found in NTP have been shown to have positive clinical effects on various diseases, which renders NTP attractive for applications in medicine. For example, wound healing, antimicrobial effects on tissues, anti-inflammatory, tissue-stimulating, and treatment of benign, pre-malignant, and malignant conditions.

A variety of different NTP devices have been developed and tested for research purposes. In general, the NTP devices can be divided into two types: a) direct discharge in which plasma is created using a dielectric barrier discharge (DBD) device; and b) indirect discharge in which plasma is created distant from the plasma formation site and carried to a distant target site via a carrier (e.g., gas, helium, argon, nitrogen, etc.) (also referred to as jet plasma).

Devices that create and deliver NTP for medical use are currently available or under development. For example, kINPen MED (INP Greifswald/neoplas tools GmbH, Greifswald, Germany) is a jet plasma device that is created in a handpiece or similar housing with the plasma transport to the target tissue site via a gas such as argon. As a further example, PlasmaDerm® VU-2010 (CINOGY Technologies GmbH, Duderstadt, Germany) is a DBD-based device that generates NTP over the target tissue site.

The generation of NTP can be summarized as ionization and excitation of atoms or molecules of a neutral gas (e.g., argon, helium, oxygen, nitrogen, air, or mixtures thereof) via electron impact in response to supplying electrical energy; interaction of electrons and high energy states of atoms or molecules with reaction partners in the plasma phase and its vicinity (ambient air, liquids, surfaces); generating secondary and tertiary reactive species; and emission of electromagnetic radiation (UV, visible light, IR/heat, electric fields)

formed by excitation and depletion processes or charge transport. Free electrons, high energy states of atoms and molecules along with ions and radicals in the plasma and those generated in secondary reactions are the main components of the chemical reactivity and biological activity of a plasma. The sum of the NTP derived chemical entities is often referred to as reactive species, for example, reactive oxygen species (ROS), reactive nitrogen species (RNS), and combination of reactive oxygen and nitrogen species (RONS), all collectively referred to as plasma generated species (PGS). The NTP has been shown to kill and distress pre-cancer and cancer cells through biochemical pathways and immunogenic response, disrupt biofilms and eradicate bacteria, spores, viruses, fungi, including multidrug resistant organisms, and promote angiogenesis and tissue regeneration through stimulation of stem cells.

FIG. 1 is a block diagram of a DBD device configuration, under an embodiment. DBD configurations and principles to create NTP are characterized by the presence of an insulating material in the discharge path. Dielectric materials such as glass, quartz, and ceramics can be used, but embodiments are not so limited. Further, DBD devices that create plasmas can be created at atmospheric pressure but are not so limited. The operation of a plasma at normal (atmospheric) pressure with moderate high voltage amplitudes uses a discharge gap approximately in the range of 0.1-10 millimeters (mm). Because of the capacitive character of the discharge arrangement, alternating or pulsed high voltage is used. The high voltage amplitude is approximately in the range of 1 to 100 kilovolts (kV).

With reference to FIG. 1, a DBD is ignited by applying a high voltage between two electrodes, wherein at least one of the electrodes is insulated by a dielectric. By using the insulation, the occurrence of an arc discharge is prevented. Instead, many fine plasma filaments usually form between the electrodes, but they only have a very short lifetime in the range of nanoseconds.

Figure 2A:
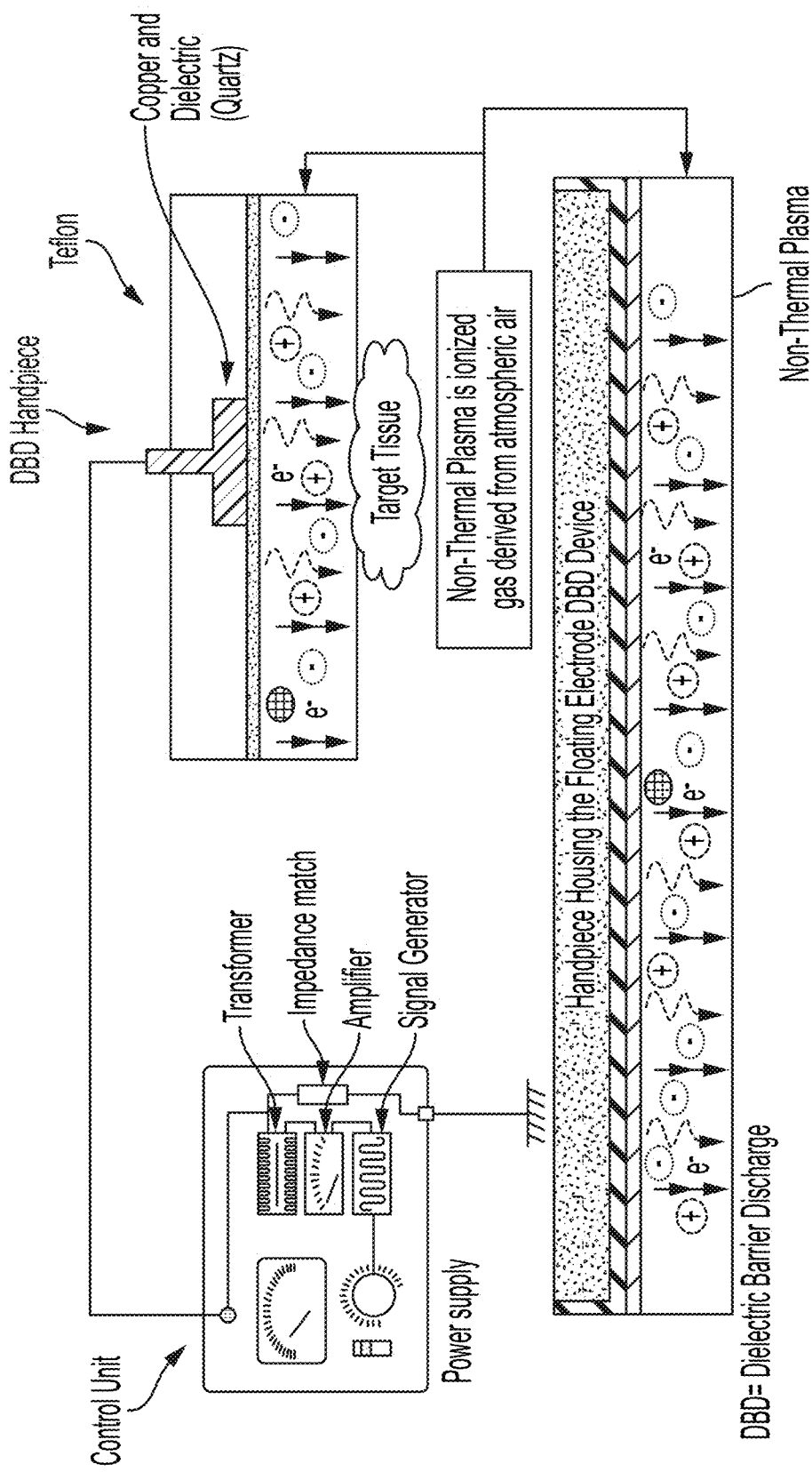
FIGS. 2A and 2B (collectively referred to herein as "FIG. 2") show plasma creation using a volume DBD based device, under an embodiment.
Figure 2B:
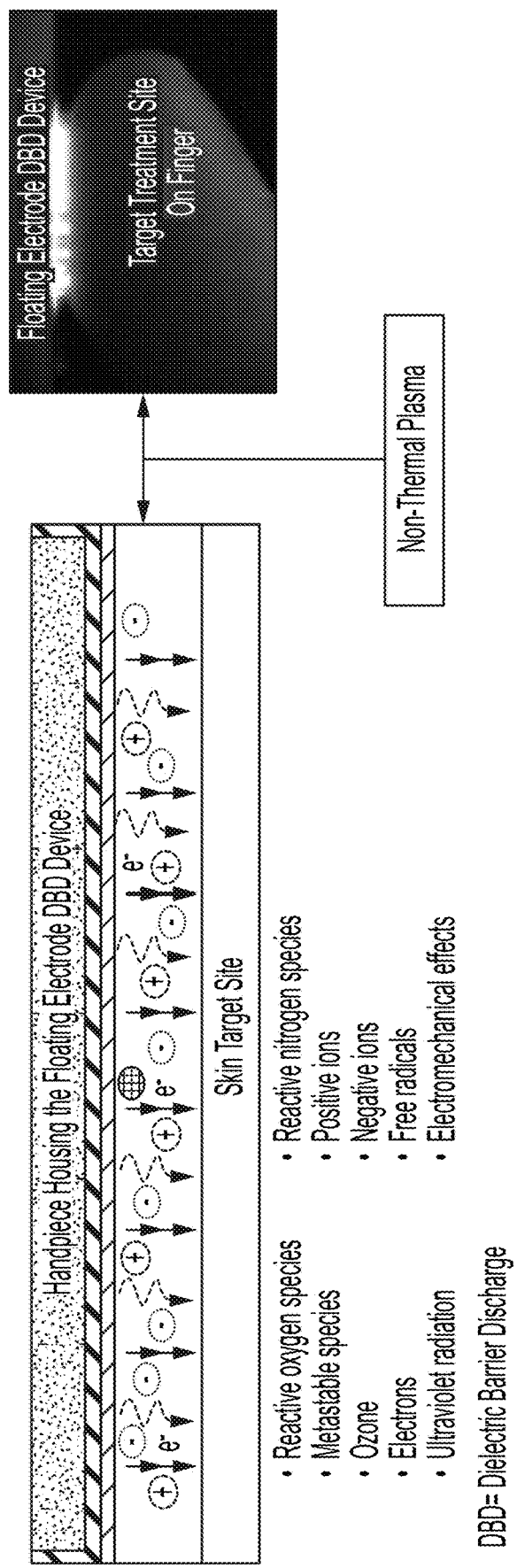

In volume DBD generated plasma, the plasma ignition occurs in a gap between an isolated high voltage electrode and the target to be treated. FIGS. 2A and 2B (collectively referred to herein as "FIG. 2") show plasma creation using a volume DBD based device, under an embodiment. Consequently, cultured cells or living tissues in biomedical application are part of the discharge electrode configuration. The DBD device configuration in this example is referred to as floating electrode DBD. Plasma has direct contact with the target to be treated and the target is directly exposed to the electrical field that is necessary for plasma generation.

In surface DBD generated plasma, plasma is ignited around an individually designed electrode structure (e.g. circular or grid-like), which is isolated from a counter electrode. There is no direct contact of the active plasma with the target to be treated, instead impact is achieved by transport processes bringing the reactive species to the living tissue. With both DBD configurations, atmospheric air serves as the working gas for plasma generation. Both volume and surface DBD devices are suitable to generate plasmas over larger areas.

Figure 3:
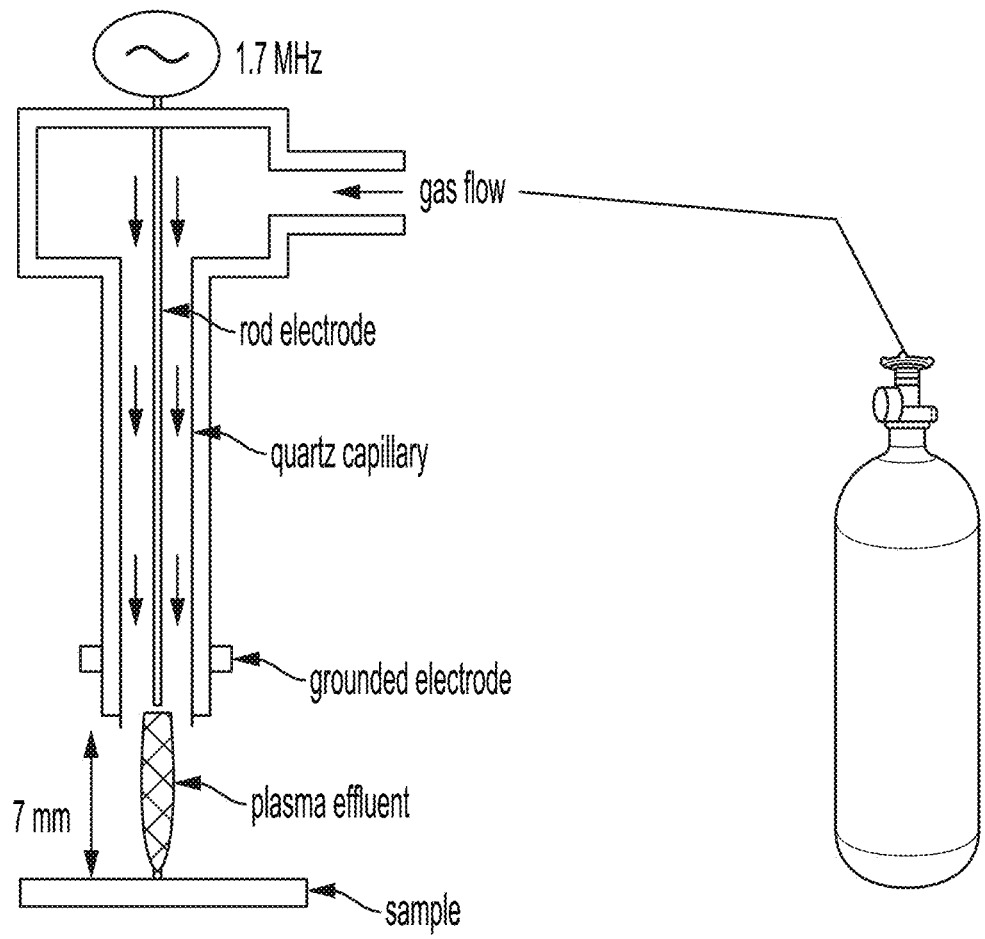
FIG. 3 is a block diagram of a jet plasma system configuration, under an embodiment.

FIG. 3 is a block diagram of a jet plasma system configuration, under an embodiment. In the jet plasma device, the electrode is configured for plasma generation distant from the tissue target site and is generally located in or around a tube-like arrangement, in most cases inside a pen-like device. Diverse electrode configurations can be used, e.g. pin electrodes, ring electrodes, plate electrodes etc. The plasma is ignited inside the device using a working gas that is flowing through the tube. The so-called plasma effluent (or afterglow) is carried out along the gas flow and can be brought into direct contact with the target to be treated. In order to maintain a low temperature and to achieve excellent controllability of the discharge, most jet plasma devices use noble gases (e.g., helium or argon) as the working gas, often doped with small amounts of molecular gases (e.g., nitrogen, oxygen). The target to be treated is not part of the electrode configuration. However, because of the conductivity of the plasma and its afterglow, small electrical currents may pass to the target. By choosing an appropriate design of electrode and high voltage waveform these currents can be easily controlled.

An example of an argon-driven atmospheric pressure plasma jet device includes kINPen. A needle electrode inside a dielectric capillary is powered with a sinusoidal high voltage (2-6 $kV_{pp}$) with a frequency of 1.0-1.1 MHz (power less than 3.5 W in the hand-held unit). Argon gas with a flow rate of 3-5 standard liters per minute (slm) is used as the working gas. The plasma is generated at the tip of the needle and is subsequently released with the feed gas flow into the atmospheric environment, thereby generating a plasma effluent having a length of approximately 9-12 mm and a diameter of approximately 1 mm. Under these conditions, the electron density in the core plasma region near the high voltage electrode tip is on the order of $10^{12}$/cc and one order of magnitude lower in the visible effluent zone. However, electron density depends on several parameters and can be varied by admixture of molecular gases, such as oxygen and nitrogen.

The reactive species generated inside the plasma or as a result of plasma interactions with the surrounding media are considered the most important components responsible for biological plasma effects. In the kINPen, the argon-based plasma effluent is exposed to atmospheric air containing predominantly oxygen, nitrogen, and water. Traces of these, especially the water, are contained in the working gas in low ppm-amounts. These atmospheric air compounds are the precursors for secondarily generated non-radical and radical reactive oxygen and nitrogen species (ROS, RNS). Generation of ROS and RNS can also be modulated by controlled admixture of oxygen, nitrogen, water or air to the argon working gas flow, or by gas shielding and modification of the atmosphere around the plasma effluent. The effluent contains ROS, RNS, and residual high energy states target a liquid (a tissue). Current knowledge assumes that at the interface between gas phase and liquid (or solid) target as well as in the target bulk a considerable rearrangement of the ROS/RNS pattern occurs. Besides interactions of the plasma derived species among themselves, the interaction with target biomolecules results in the formation of diverse chemical structures.

Because all plasma sources for biomedical applications are working under atmospheric air conditions or use ambient air as working gas, the generation of ROS and RNS from air-based oxygen and nitrogen is a corresponding feature of all these plasma sources. However, the composition and quantity of plasma-generated ROS and RNS, as well as UV irradiance, electrical field and other characteristics, are strongly dependent on specific plasma sources and device parameters as working gas composition, power input and temperature.

The biological effects of NTP's are mainly based on ROS and RNS, which is primarily reasoned from experimental observations in vitro. Plasma effects on mammalian cells were found to be dependent on cell culture media composition, each exhibiting a different antioxidative potential. A multitude of investigations on plasma-liquid interactions has demonstrated the occurrence of ROS and RNS in liquid phases following plasma treatment. Moreover, it has been shown several times that liquids, such as water, physiological saline, or cell culture media become biologically effective following plasma treatment. This underlines a key role of liquid phase composition for biological plasma effects. ROS and RNS like superoxide ($O_2$—•), hydrogen peroxide ($H_2O_2$), hydroxyl radical (•OH), singlet oxygen (lO2), ozone (O3), and RNS, such as nitric oxide (•NO), nitrogen dioxide (•NO2) and peroxynitrite (ONOO—), are transferred from plasma into the liquid environment of cells and tissue, or they are generated by a very complex network of secondary liquid reactions.

This insight of the central role of ROS and RNS has opened up the door to the field of redox biology to explain and interpret biological effects caused by NTP. Redox biology can be taken as the interface between the more or less unspecific impact of external factors and the specific response and adaptation of a cell or an organism via its metabolic and macromolecular structures. Meanwhile, it is well known that ROS and RNS are not solely harmful in cells, but also serve as signaling molecules via reversible oxidations and reductions of specific protein structures with cysteine as a major reaction target.

Depending on plasma treatment intensity and time, it is possible to inactivate mammalian cells by initializing programmed cell death in them. This is true particularly for cancer cells. After several reports on apoptosis induction in cancer cells in vitro, animal studies on transcutaneous plasma treatment of subcutaneously induced solid tumors could prove the general concept of plasma-supported tumor treatment. However, there are several open questions about the mechanisms of plasma attack on cancer cells, and possible selectivity with regard to healthy tissue or on possible secondary effects distant from the region of local plasma treatment. Most current hypotheses are based on a predominant role of plasma-generated redox active species. Briefly, it is assumed that NTP treatment causes apoptosis of cancer cells through a selective rise of intracellular ROS and corresponding ROS-based death pathways. In that regard, enhanced sensitivity of cancer cells may be caused by enhanced ROS levels in the cancer resulting from its unique metabolic activities.

Another hypothesis is based on the specific action of NTP via singlet oxygen generation and the subsequent induction of intercellular ROS-RNS-dependent apoptosis-inducing signaling. Plasma has been shown to induce proapoptotic effects more efficiently in tumor cells compared with the benign counterparts, leads to cellular senescence. In published in vivo clinical reports, plasma has been shown to reduce skin tumors. Plasma has also been shown to be effective in treating benign, pre-malignant, and cancerous skin conditions.

Embodiments described herein increase plasma generated species (PGS) over the target and in the target tissue, and include but are not limited to one or more of the following: hydrating the tissue target (for example skin) before plasma treatment; improving the gas permeability of the tissue target by applying a PFC and PFC emulsion with dissolved gases such as oxygen, nitrogen, and combinations of gasses thereof; increasing the partial pressure of select gasses such as nitrogen and oxygen in the target tissue by applying a PFC emulsion with dissolved select gasses to the target tissue; increasing the outgassing and number of select gasses at the atmosphere-tissue interface; and applying SSOE to skin and apply DBD plasma for example and create enhanced production of plasma generated species (PGS).

More particularly, an embodiment increases PGS by applying perfluorocarbon (PFC) emulsions containing high concentrations of dissolved gasses or combinations of dissolved gasses such as oxygen and/or nitrogen to penetrate tissues and increase the tissue concentration or partial pressure of delivered gas(ses). An alternative embodiment increases PGS by applying PFC topically to tissues to increase the solubility of plasma into the tissues. Another alternative embodiment increases PGS by applying PFC emulsions containing water to hydrate tissues.

Supersaturated Gas Emulsion (SSGE)

The SSGE comprises a dispersed phase of perfluorocarbon (PFC) droplets encapsulated within an aqueous continuous phase. Perfluorodecalin (PFD), a PFC, is selected for its high oxygen solubility, chemical inertness, and biocompatibility, but embodiments are not so limited. FIG. 4 shows a table including the component ingredients in an example embodiment of the SSGE, including water, perfluorodecalin, glycerin, phospholipids, Polawax, Vitamin E, and preservative, under an embodiment.

Gasses such as oxygen and nitrogen, which are not listed in this table, are added during the manufacturing process and after emulsification. The gas content of SSGE in the pressurized canister is dependent on the PFD concentration and the gas charging pressure used in the manufacture of the emulsion. The gas content of SSGE increases linearly with charging pressures. For example, if oxygen is used, the standard processing conditions for SSGE with oxygen as the gas calls for oxygenation at elevated pressures of at least 180 psig (charging pressure) of medical grade oxygen (created supersaturated oxygen emulsion or SSOE). The final equilibrium concentration of dissolved oxygen at 180 psig is approximately 1.8 ml $O_2$ (STP) per ml of emulsion. As a point of comparison, water at ambient conditions contains approximately 0.006 ml $O_2$ per ml water.

In this embodiment using oxygen, the SSOE is packaged under pressure to maintain the level of dissolved oxygen in solubilized form. The container pressure must be equal to or greater than the oxygenation pressure to prevent outgassing. When SSOE is dispensed, oxygen is outgassed from the emulsion and exposes a target tissue, for example skin, to oxygen.

In a current packaging configuration, SSOE, for example, comprises a pressurized canister containing 37 grams of SSOE. Each gram of SSOE includes approximately 1.8 ml of dissolved oxygen. Dispensing one gram of SSOE topically on the skin provides 1.8 ml of oxygen. Upon application, oxygen will diffuse from the SSOE into its ambient surroundings including the skin.

Figure 5:
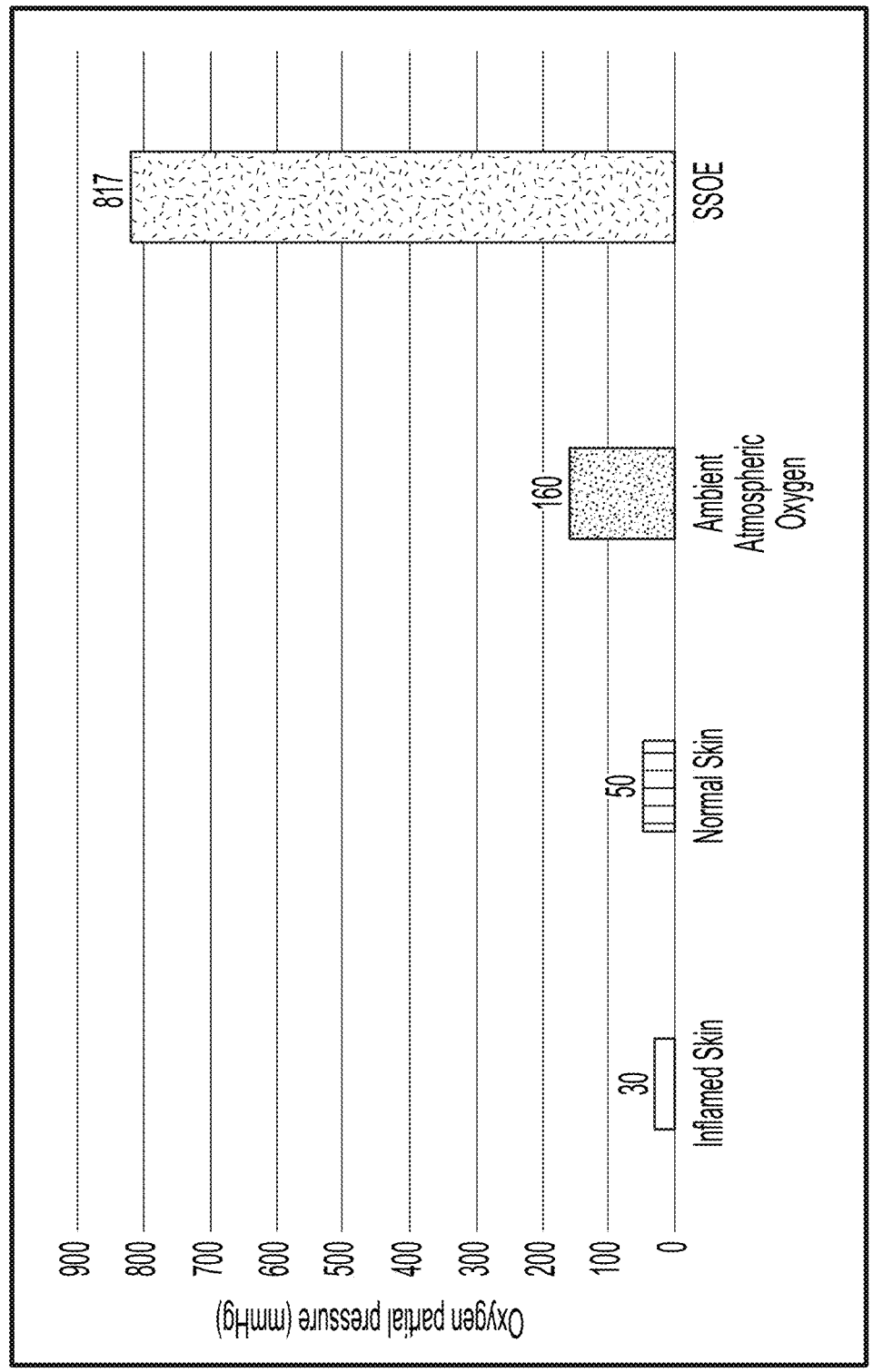
FIG. 5 shows a comparison of the pO$_2$ of hypoxic tissue, normal skin, ambient atmospheric oxygen, and SSOE, under an embodiment.

FIG. 5 shows a comparison of the $pO_2$ of hypoxic tissue, normal skin, ambient atmospheric oxygen, and SSOE, under an embodiment. In this comparison, the partial pressure of oxygen ($pO_2$) of air at one atmosphere (760 mmHg) is approximately 160 mmHg (21% oxygen). Normal $pO_2$ of arterial blood is approximately 100 mmHg. Normal tissue oxygen partial pressures range from 100 mmHg in pulmonary alveoli to 20 mmHg in liver parenchymal cells. Inflamed acute and chronic wounds can have oxygen tension levels ($pO_2$) between 0 and 30 mmHg even when surrounding subcutaneous $pO_2$ levels are on the order of 30 to 50 mmHg. Normal cell metabolism can be impaired at $pO_2$ levels of under 20 mmHg. FIG. 1 also shows the $pO_2$ of SSOE compared to other topical products and conditions.

Figure 6:
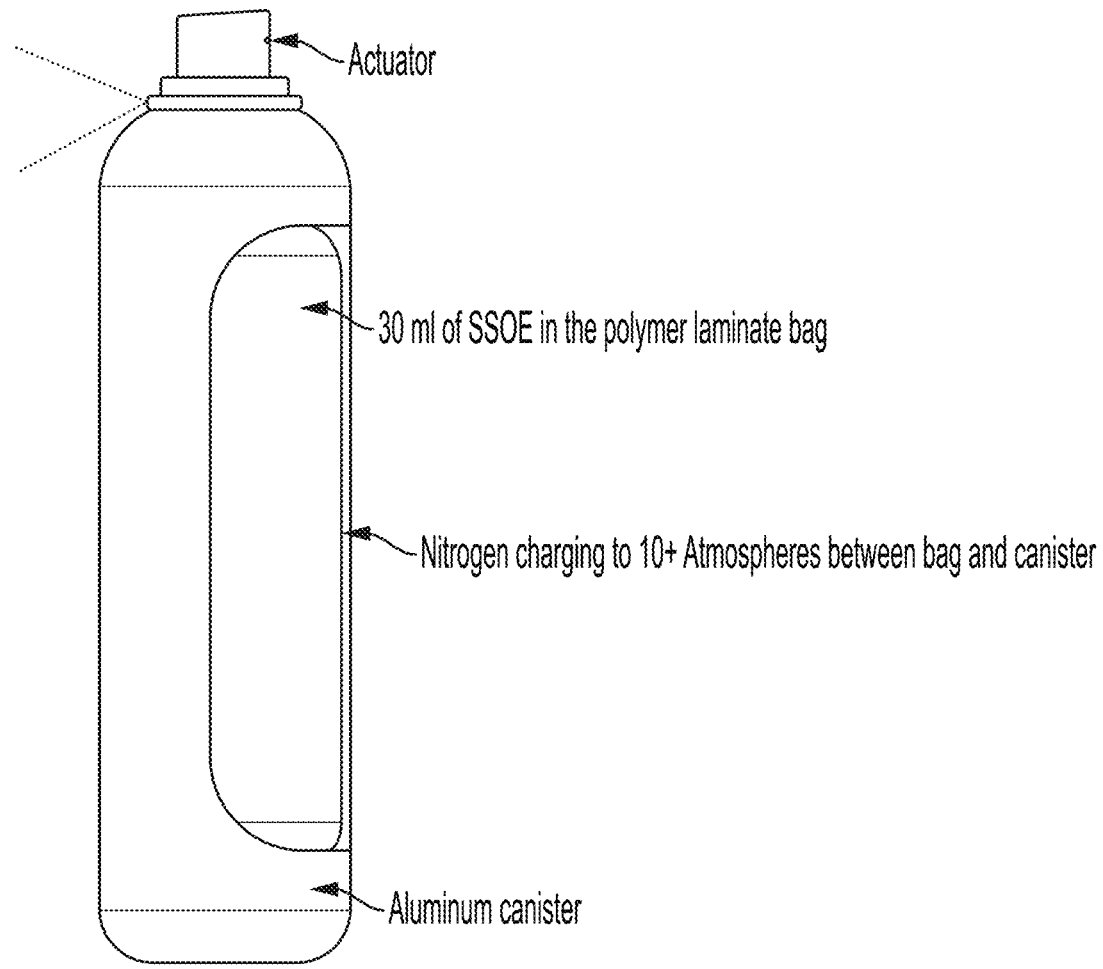
FIG. 6 shows an example of SSOE canister packaging, under an embodiment.

SSOE Pressurized Canister FIG. 6 shows an example of SSOE canister packaging, under an embodiment. In this configuration, SSOE is packaged in a pressured bladder canister including 1.0 ounce volume (29.6 ml volume or 37 grams by weight). The bladder canister comprises an empty bladder with an internal canister pressure of 175±5 psig. During the manufacturing process, the SSOE is pumped into the bladder of the canister, resulting in an intra-canister pressure of approximately 230 psig. Since the canister is pressurized, the oxygen remains in the SSOE.

The SSOE is not an aerosol propelled product. Rather, a hermetically sealed bladder (pouch) inside the canister is filled with the SSOE while pressurized nitrogen gas surrounds this bladder. When the nozzle of the SSOE can is actuated, the gas in the canister squeezes the bladder and causes the SSOE to be discharged uniformly from the canister. All surfaces of the packaging that contact the SSOE either during its storage or delivery are non-reactive biocompatible materials. The bladder materials are FDA-compliant and keep the SSOE separated from the nitrogen gas propellant. The bladder consists of a laminated structure of polypropylene on the product contact side, a center layer of aluminum foil, and a PET (polyethylene terephthalate) outer layer.

PFD Emulsion Formulation

Figure 7:
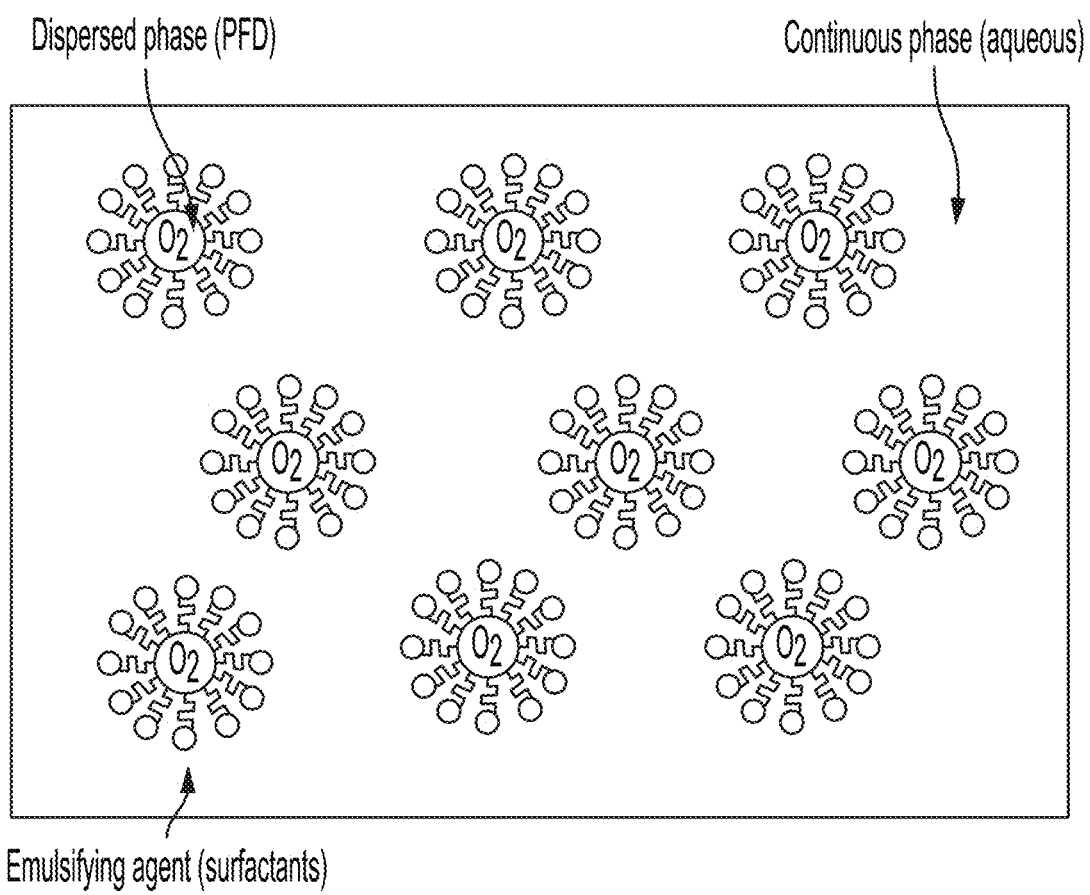
FIG. 7 is an example depiction of the SSOE including dissolved oxygen concentrated in high-solubility PFD droplets that are stabilized by emulsifying agents within an aqueous base, under an embodiment.

SSOE comprises a dispersed phase of PFD droplets encapsulated within an aqueous continuous phase. The chemical ingredients of the emulsion (e.g., see FIG. 4) include PFD, water, humectants, lubricity enhancers, and emulsion stabilizers (surfactants). PFD is chosen for its high oxygen solubility and chemical inertness. Mechanical agitation and homogenization of the heated ingredients forms a stable suspension of PFD microdroplets within the aqueous base. This emulsion is thermally and mechanically stable and will not separate into its constituent phases unless subjected to extreme conditions. FIG. 7 is an example depiction of the SSOE including dissolved oxygen concentrated in high-solubility PFD droplets that are stabilized by emulsifying agents within an aqueous base, under an embodiment. Small, discrete PFD droplets, shown in white, are depicted within the continuous aqueous phase, shown in blue. A surfactant shell surrounds each PFD droplet, encapsulating the dispersed PFD with a complex lamellar structure of surface-active stabilizers. These protective shells act to repel one another within the emulsion, preventing the microdroplets from coalescing and thereby imparting stability to the emulsion. Oxygen in the example of SSOE is added at high concentration during a secondary process after emulsification.

Oxygen Content

The oxygen content of the packaged SSOE is determined primarily by PFD content (oxygen solubility of is approximately 10-20 times greater than water) and oxygen charging pressure during manufacture. The standard processing conditions for SSOE calls for oxygenation of at least 180 psig resulting in an equilibrium concentration of dissolved oxygen on the order of 1.8 ml $O_2$ (STP)/ml of SSOE, or three hundred (300) times the amount of oxygen contained in a glass of water.

The SSOE must be packaged under pressure for the dissolved oxygen to persist in solubilized form. The canister pressure must be equal to or greater than the oxygenation charging pressure to prevent outgassing of the oxygen from the emulsion.

SSOE Bench Testing

Figure 8:
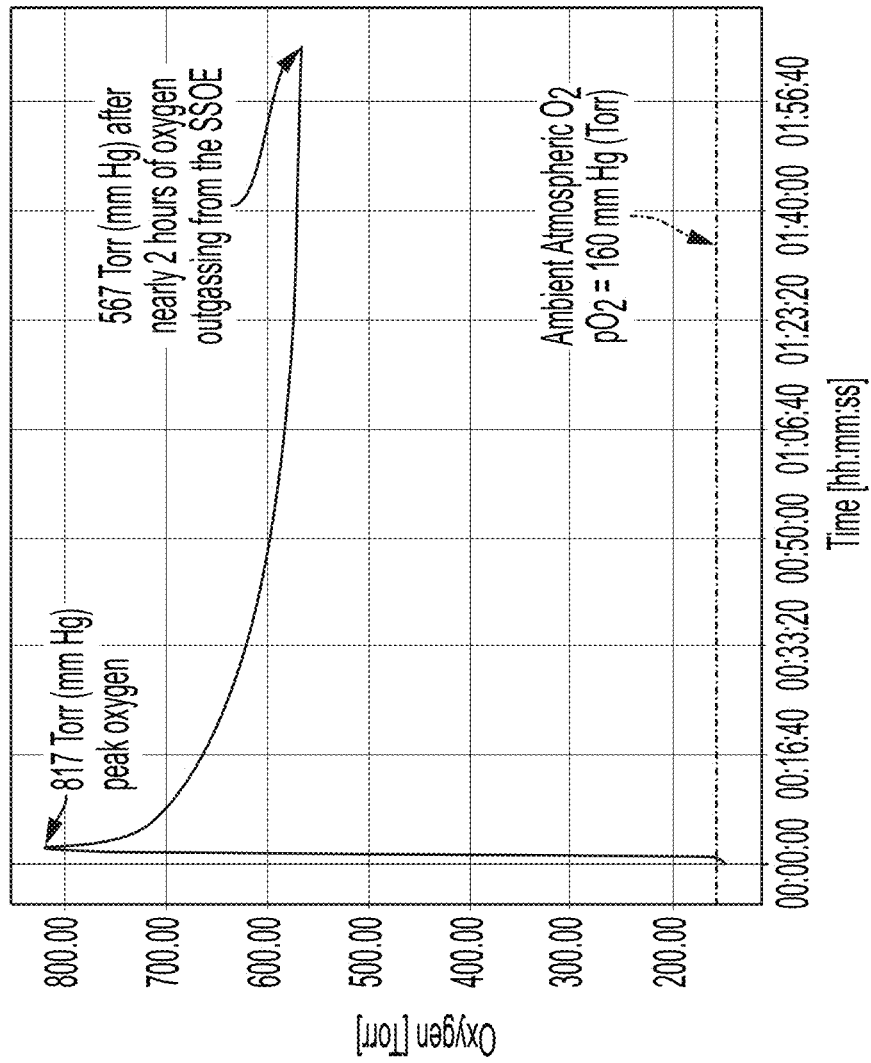
FIG. 8 includes a graph showing the oxygen outgassing of SSOE along with measurement of the oxygen partial pressure within the SSOE, which peaks at 817 mm Hg, under an embodiment.
Figure 8:
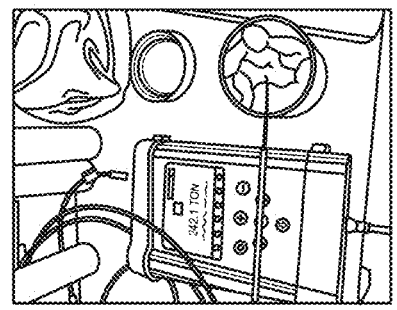

FIG. 8 includes a graph showing the oxygen outgassing of SSOE along with measurement of the oxygen partial pressure within the SSOE, which peaks at 817 mm Hg, under an embodiment. The oxygen partial pressure in this example was measured using a fiberoptic oxygen sensor. After nearly two hours, the oxygen outgassing continued as was found to be at 567 mmHg.

Figure 9:
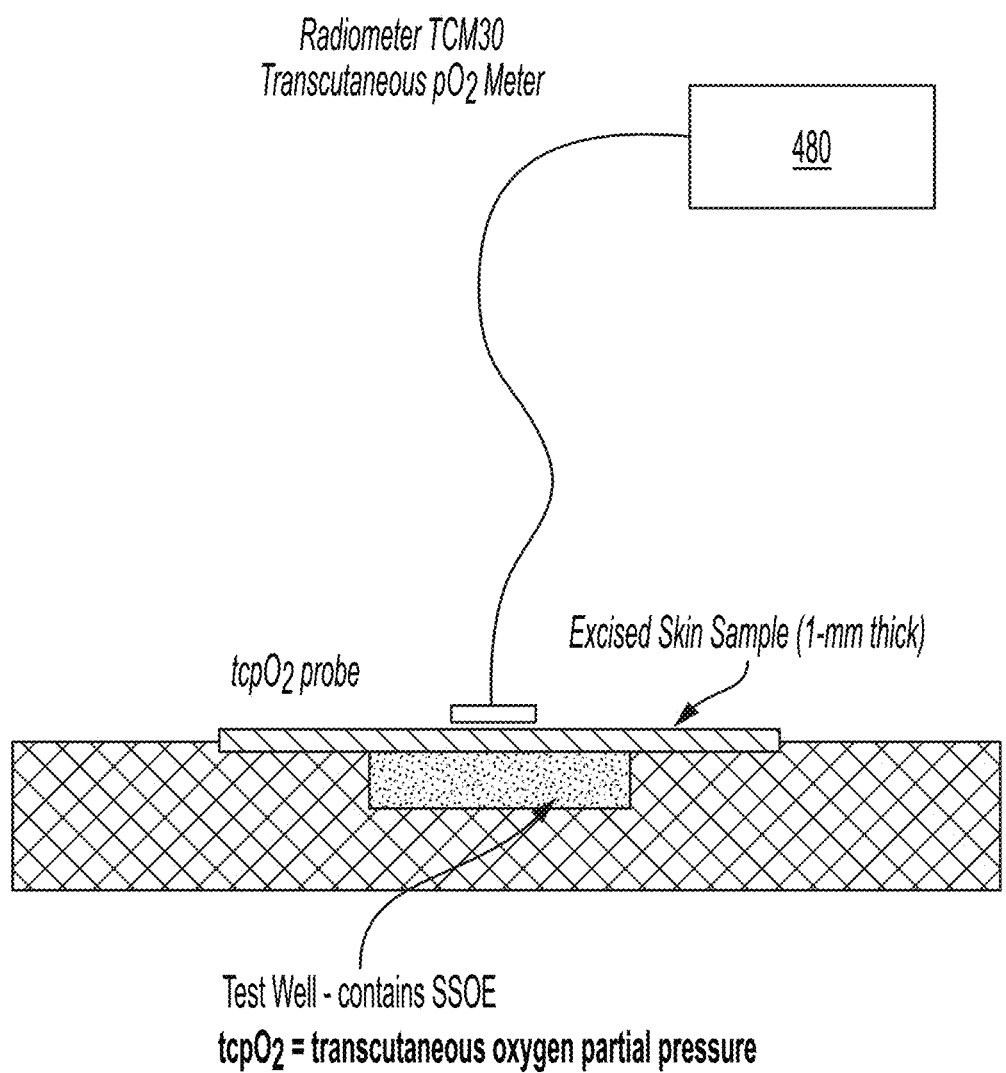
FIG. 9 shows a bench testing configuration to measure the flow oxygen from SSOE across 1 mm of porcine skin, under an embodiment.

Bench testing was completed to measure the oxygen transfer from the SSOE to skin. FIG. 9 shows a bench testing configuration to measure the flow oxygen from SSOE across 1 mm of porcine skin, under an embodiment. In this example test, approximately 2.0 ml of SSOE was placed in a test well measuring 2.5×2.5×0.3 cm (depth). The test well was covered by a layer of epidermis of excised, non-viable porcine skin. The epidermis and underlying dermis was trimmed to a uniform thickness of approximately 1 mm over the area of the test well. A transcutaneous $pO_2$ probe was placed on the porcine skin over the test well containing the emulsion. The oxygen concentration in the tissue was measured over time with a standard transcutaneous $pO_2$ probe (Radiometer TCM) applied to the skin surface opposite the applied emulsion. The skin tissue $pO_2$ is equilibrated with ambient surroundings at time zero and rises over time as the diffusing oxygen from the emulsion penetrates through the porcine skin.

Figure 10:
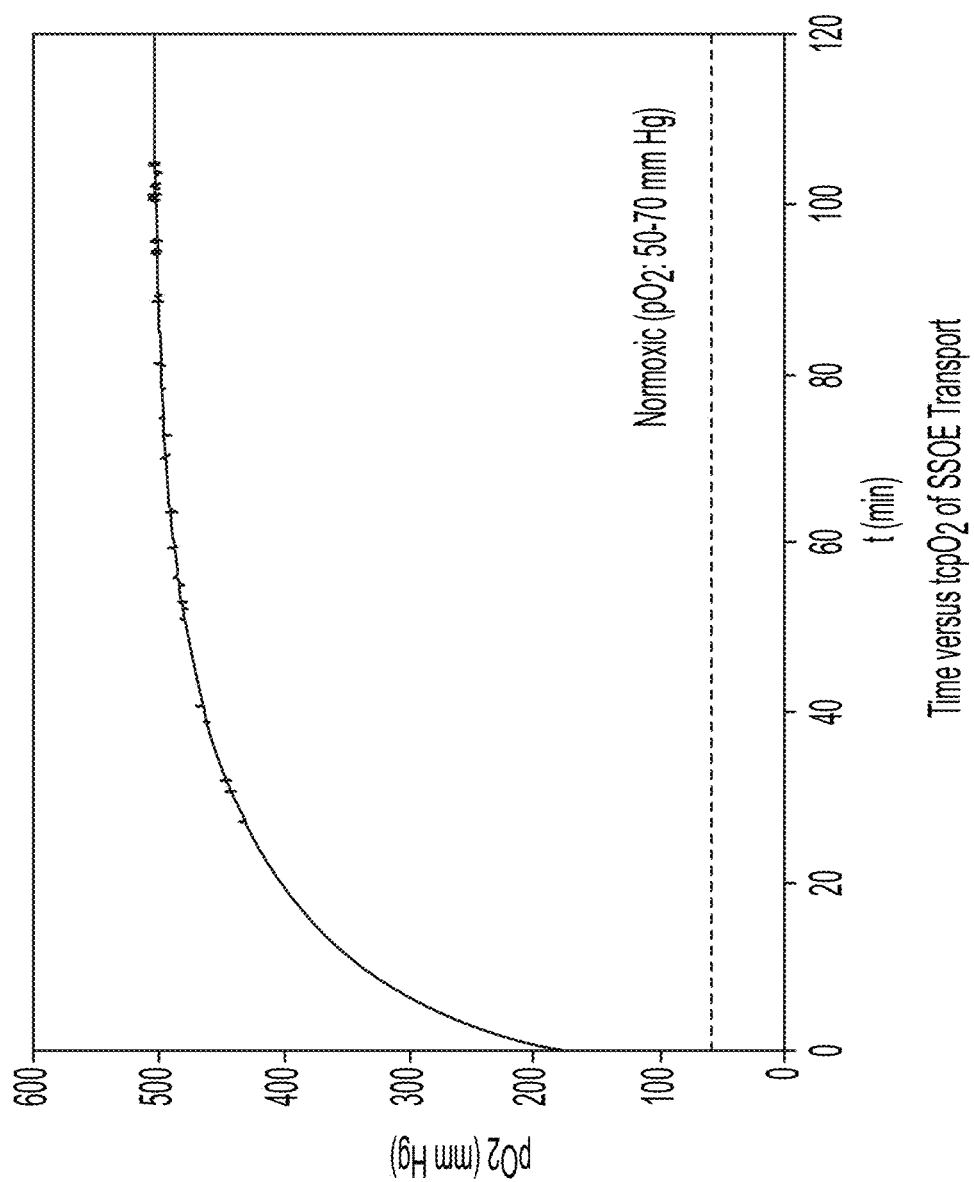
FIG. 10 shows the oxygen transfer data of the bench testing, including time versus transcutaneous partial pressure of O$_2$ (tcpO$_2$) across 1 mm of excised porcine skin, under an embodiment.

FIG. 10 shows the oxygen transfer data of the bench testing, including time versus transcutaneous partial pressure of $O_2$ ($tcpO_2$) across 1 mm of excised porcine skin, under an embodiment. Oxygen transfer from the SSOE occurs via diffusion (concentration gradient) and convection (mass transfer by absorption). The tissue oxygenation level, or $pO_2$, is monitored after the SSOE is applied at time zero. After a few minutes, a sharp increase in oxygenation is observed from ambient conditions to an elevated, sustained peak value approaching 500 mmHg. Because the skin sample is excised and non-absorbent, the oxygenation level can be sustained for many hours after only one SSOE application.

On skin samples greater than twice this thickness (1 mm), SSOE has demonstrated that the oxygenated emulsion penetrates the tissue and elevates $pO_2$ levels for a sustained period. These bench tests coupled with clinical measurements of transcutaneous partial pressure of oxygen ($tcpO_2$) after application of SSOE and combined with other corollary data, show proof that the technical goal of delivering and achieving a local hyperbaric environment.

SSOE Oxygen Transfer

Because the partial pressure of $O_2$ in the SSOE is greater than that in atmospheric air, a gradient exists between the SSOE and the atmosphere. Once dispensed from the canister, oxygen slowly begins to move out of the PFD emulsion, through the phospholipid membrane, and through the water of the SSOE down the gradient via the process of diffusion. The oxygen preferentially leaves the SSOE through surfaces of the emulsion in contact with tissue or air. Because of the slow nature of the diffusion process, release of oxygen from the SSOE is very gradual. A layer of SSOE approximately 3 millimeters is capable of delivering oxygen to a contacting tissue surface at levels above those found in arterial blood for at least several hours. For example, in the treatment of burn, if 2 ml of SSOE is topically applied, approximately 4 to 5 ml of oxygen is available, much of which is delivered to the covered tissue and over a period of at least an hour.

The SSOE is a biocompatible emulsion that creates a local hyperoxic environment in skin. The SSOE absorbs readily into the skin for maximum oxygen delivery. After topical application, skin interstitial $pO_2$ increases 3 to 5 fold from 20 to 35 mm Hg $pO_2$ pre-application to 100 mm Hg $pO_2$ post-application (FIG. 10)

Oxygen transfer from the SSOE into the skin occurs via diffusion and convection. Diffusion describes the molecular migration of oxygen from the SSOE into the skin, and is proportional to the large oxygen concentration gradient between the applied emulsion and skin tissues. Duration of effect over hours has been observed in vitro, due to the characteristically slow diffusion process. A second important oxygen transfer process occurs via convection, wherein the SSOE is absorbed directly into the skin and transports the solubilized oxygen directly to the tissues. Rapid absorption of the SSOE, which occurs on a time scale much faster than diffusion, ensures efficient delivery of the SSOE's oxygen load to the application area.

The combination of diffusive and convective transfer maximizes the effective dose of oxygen to the skin while minimizing the amount of oxygen lost to the ambient surroundings during dispensation and delivery. The SSOE formulation can be modified for rapid or slow, sustained absorption depending upon the desired rate of oxygen transfer.

SSOE Clinical Measurements

Figure 11:
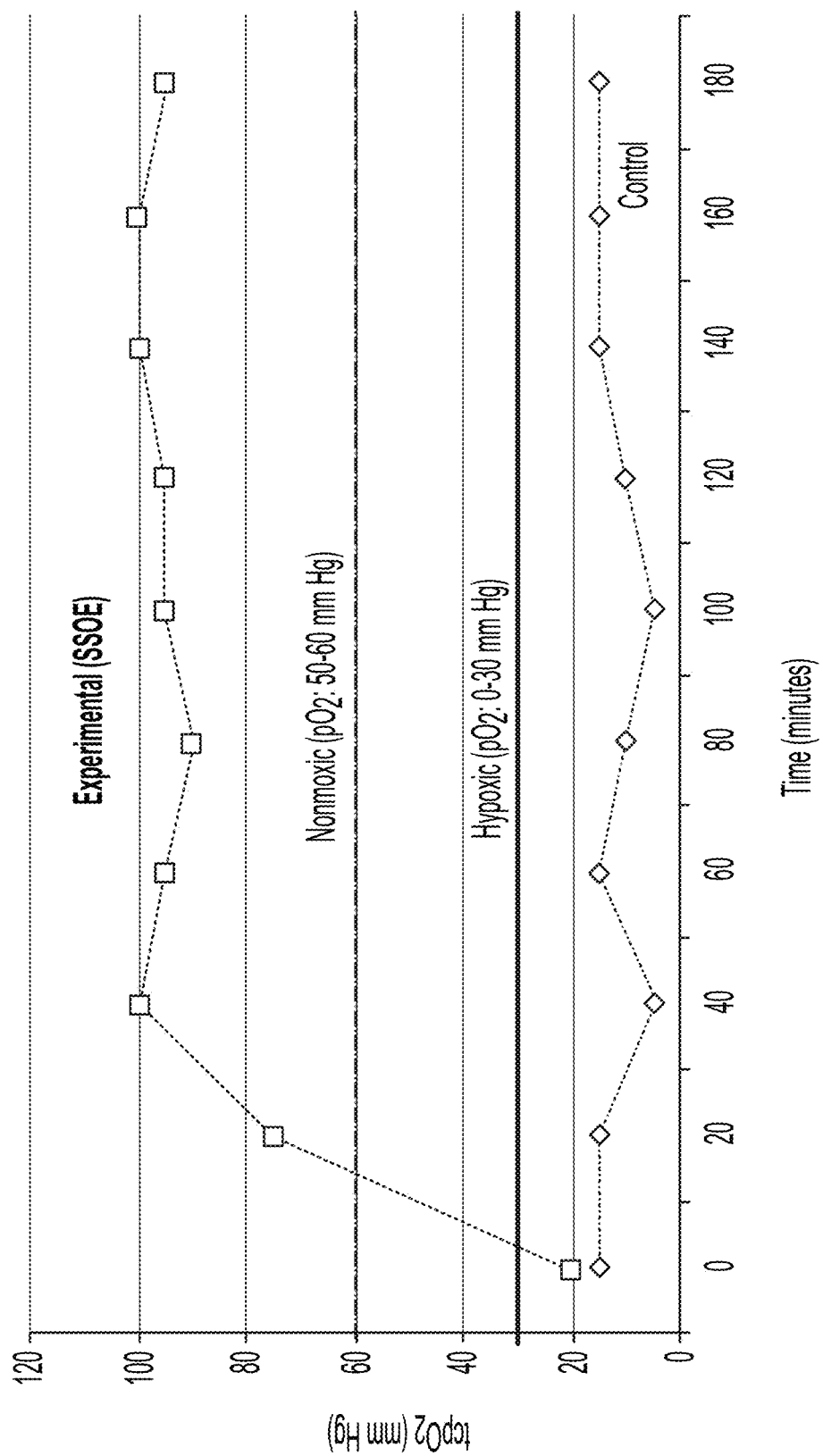
FIG. 11 shows a plot of time versus transcutaneous partial oxygen partial pressure (tcpO$_2$) of the control (post-face lift skin) and experimental (application of SSOE to post-face lift skin) on the contralateral side, under an embodiment.

FIG. 11 shows a plot of time versus transcutaneous partial oxygen partial pressure (tcpO$_2$) of the control (post-face lift skin) and experimental (application of SSOE to post-face lift skin) on the contralateral side, under an embodiment. The tcpO$_2$ increases five-fold from approximately 20 mmHg tcpO$_2$ (control) to 100 mmHg tcpO$_2$ after the application of SSOE to immediate post-face lift skin (experimental). The data in this plot represents the decrease in skin oxygen tension following facelift surgery. Oxygen tension was measured at 15 mmHg, which is a much lower when compared to pre-operative measure levels of 60 mmHg. The subsequent 5-fold increase following the application of SSOE shows oxygen transfer from SSOE to skin.

The cutaneous uptake of atmospheric oxygen contributes significantly to the oxygen supply of human dermis and epidermis. The upper skin layers to the depth of 250 μm to 400 μm are almost exclusively supplied by external oxygen, where the oxygen transport of the blood has a minor influence. SSOE delivers over 800+ mmHg of oxygen topically to skin, which is a 20+ fold increase in oxygen compared to hypoxic skin such as chronic wounds or injured skin.

SSGE in Combination with NTP

Embodiments described herein use NTP with SSGE to generate a cloud of RONS over target tissue and facilitate transport of RONS across cell membranes to disrupt internal cellular function and biochemical pathways, leading to cell death (apoptosis). The NTP system comprises a control unit comprising a power supply, control panel, and software. A DBD handpiece couples to the control unit and houses or carries the DBD electrode as described in detail herein. The DBD handpiece includes two configurations including a pencil-shaped configuration to treat single lesions, and a cylindrical-shaped configuration to treat large lesions (field treatment). The NTP system of embodiments also includes a consumable comprising a disposable, single-use polymer endcap for the handpiece. The handpiece of the NTP system creates NTP at the target site under conditions of room temperature and ambient atmosphere, and results in no thermal tissue damage. Treatment sites include sites with small and large surface areas, and treatment times are approximately one to two minutes per treatment site.

Examples are now presented showing various SSGE embodiments in combination with NTP.

Topical SSGE Application on a Lesion Before NTP Treatment

Figure 12:
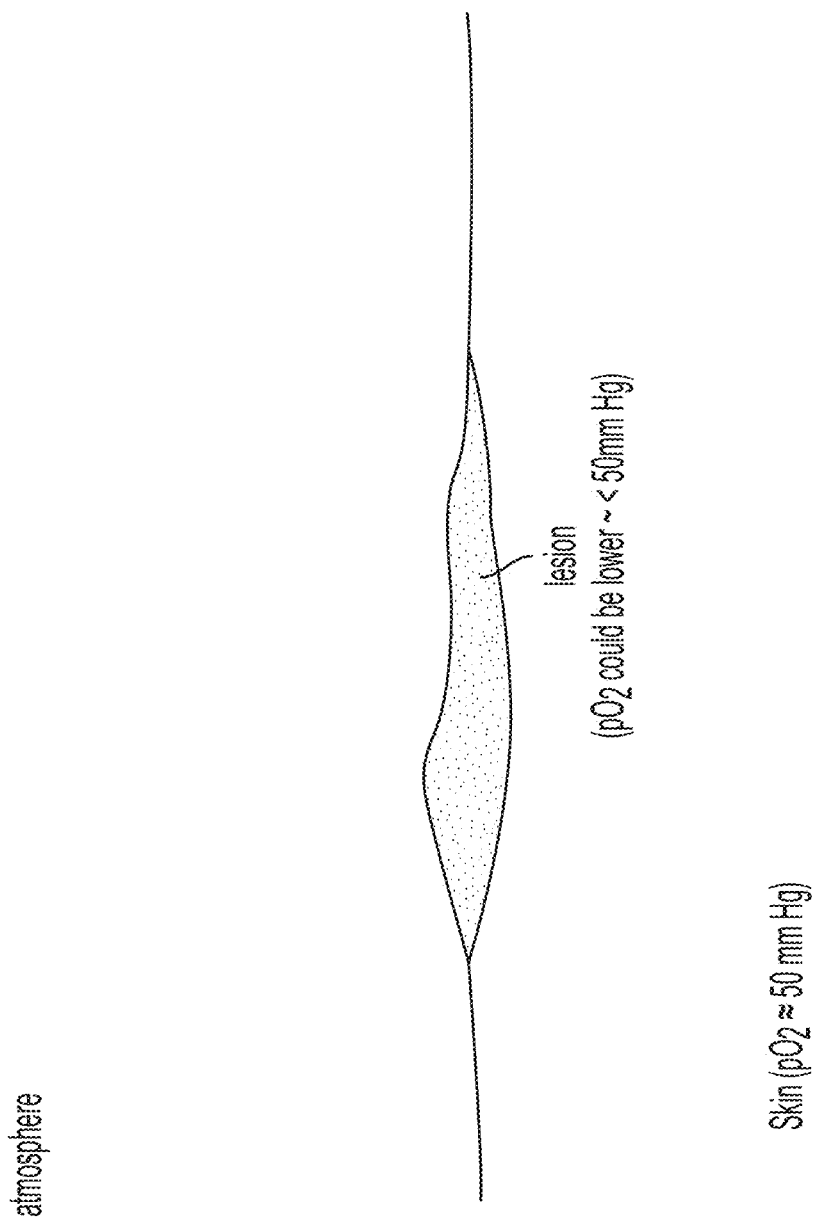
FIG. 12 shows an example skin lesion presented for treatment, under an embodiment.

An example includes treatment of a skin lesion such as actinic keratosis or skin cancer using NTP. FIG. 12 shows an example skin lesion presented for treatment, under an embodiment.

Figure 13:
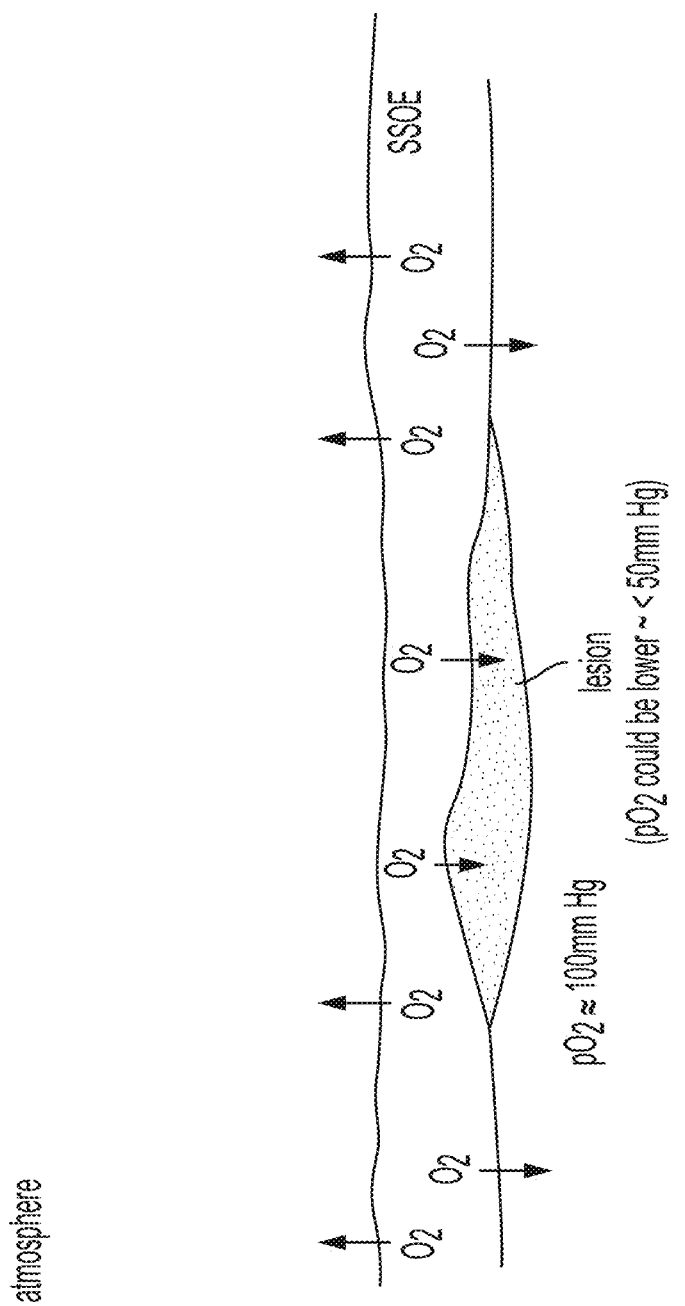
FIG. 13 shows the example skin lesion with SSGE topically applied over the lesion, under an embodiment.

Before NTP treatment, SSGE is topically applied over the skin lesion and the area to be treatment. FIG. 13 shows the example skin lesion with SSGE topically applied over the lesion, under an embodiment. In this example, SSOE is applied to increase the presence of oxygen within the skin and immediately over the skin at the atmosphere-skin interface. The SSOE is applied to the lesion for seconds to minutes. If the physician elects to increase the presence of nitrogen, a supersaturated nitrogen emulsion (SSNE) would be applied. If a combination of oxygen and nitrogen are desired, then a desired mixture of nitrogen and oxygen gas would be used in the manufacture of the SSGE resulting in a supersaturated nitrogen-oxygen emulsion (SSNOE) NTP treatment.

Figure 14:
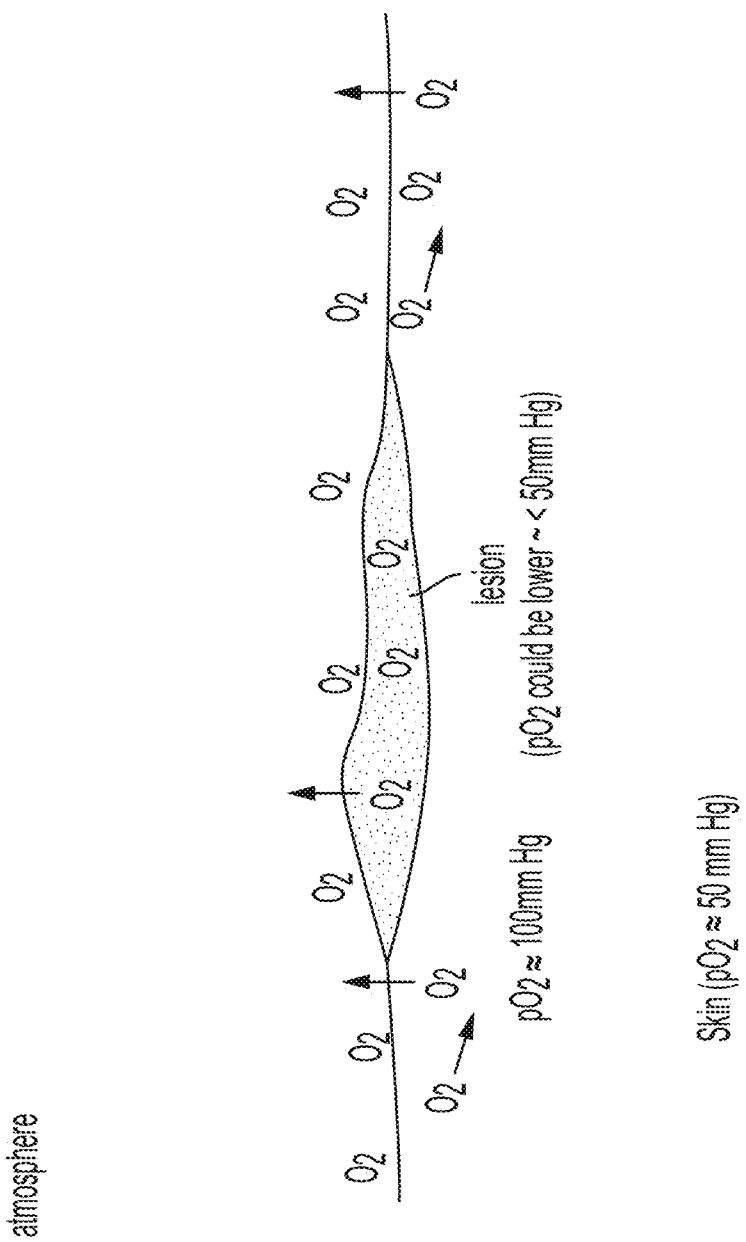
FIG. 14 shows the example skin lesion following removal of the topical SSOE prior to the NTP treatment, under an embodiment.

Immediately before NTP treatment, the SSOE can be wiped away with NTP treatment to immediately follow. FIG. 14 shows the example skin lesion following removal of the topical SSOE prior to the NTP treatment, under an embodiment.

Figure 15:
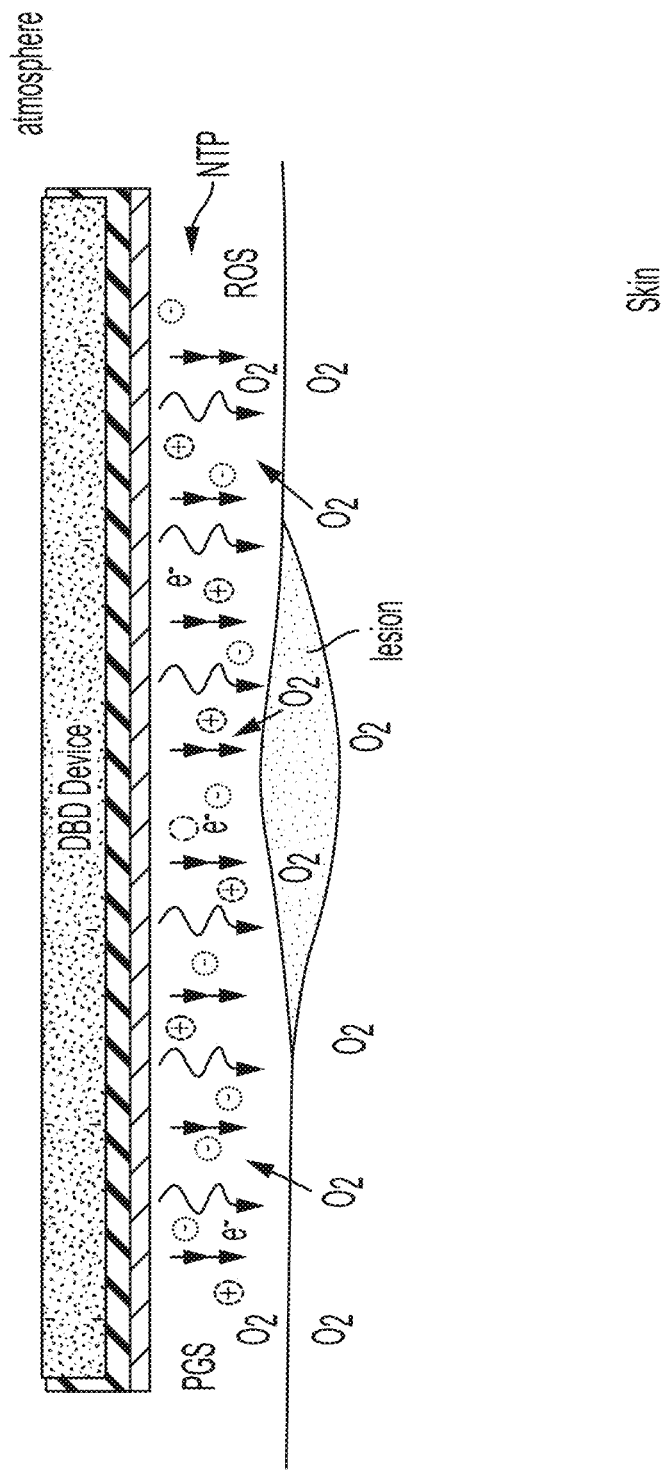
FIG. 15 shows the example skin lesion during the NTP treatment, under an embodiment.

FIG. 15 shows the example skin lesion during the NTP treatment, under an embodiment. The increased oxygen during NTP treatment increases the concentration of ROS. In addition, the PFD based SSOE is absorbed and adsorbed into the skin, wherein the PFD increases permeability and solubility of oxygen across the skin including ROS and other PGS. Furthermore, high water content of the SSOE increases the hydration of the skin, which improves the flow of PGS into the skin and lesion.

Figure 16:
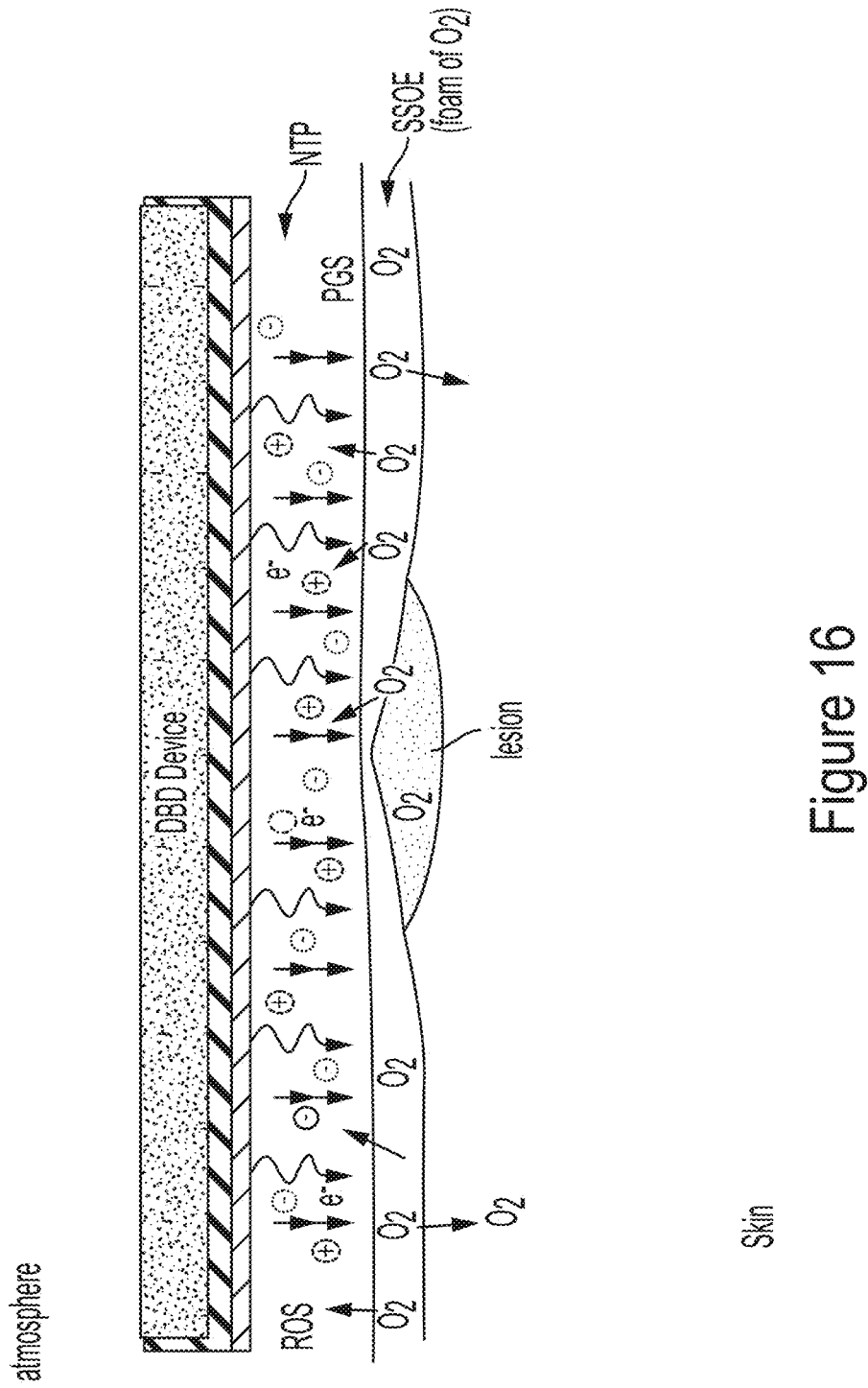
FIG. 16 shows the example skin lesion with at least a portion of SSOE remaining over the lesion for the NTP treatment, under an embodiment.

Alternatively, instead of wiping away the SSOE prior to the NTP treatment, the SSOE can be left in place or slightly removed leaving a thin layer or film of SSOE over the lesion. FIG. 16 shows the example skin lesion with at least a portion of SSOE remaining over the lesion for the NTP treatment, under an embodiment. As the oxygen outgasses from the SSOE, the SSOE expands into a porous, supersaturated oxygen foam over the lesion. The application of the NTP treatment over the thin film of SSOE covering the lesion increases the concentration of ROS and other PGS in the foam and over the lesion, allowing for improved ROS and PGS availability and delivery.

SSGE Application to Interior Wall of DBD Handpiece Cylindrical Fitting

Figure 17:
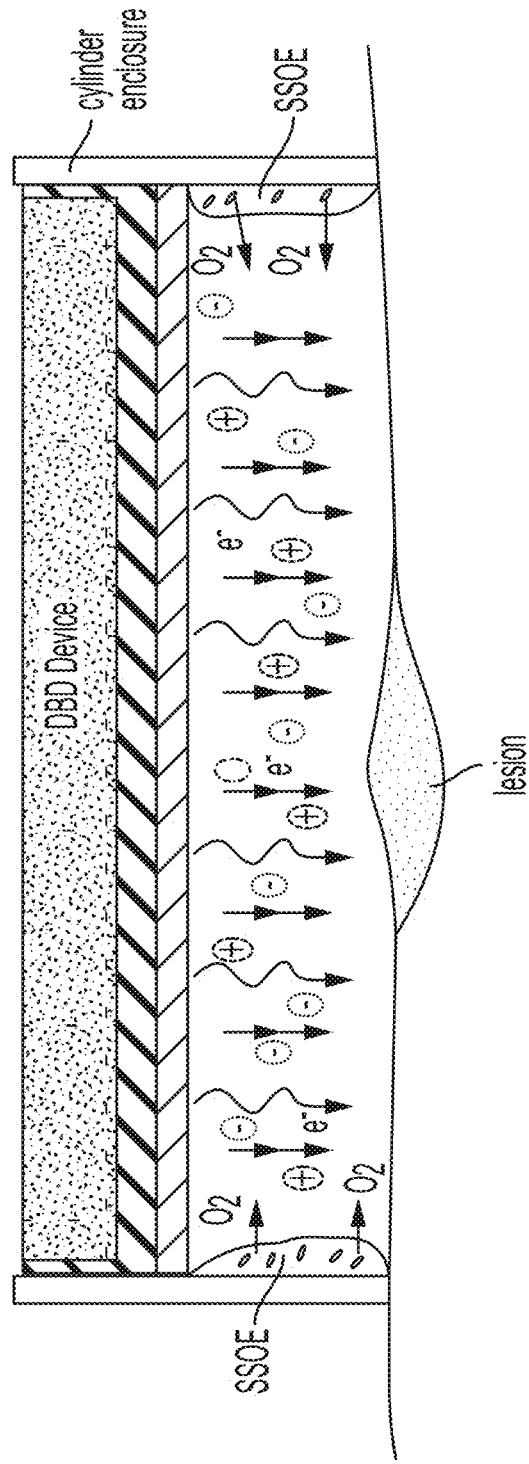
FIG. 17 shows a cylindrical fitting coupled at the distal end of the DBD handpiece and including SSOE topically placed on an interior wall of the cylindrical fitting, under an embodiment.

In the delivery of DBD NTP, the distance between the distal end of the DBD handpiece and the skin or target site should be kept at a relatively constant distance. Specifically, in an example of a cylindrical DBD handpiece, a reversible coupled cylindrical fitting can be placed at the distal end of the DBD handpiece to provide a desired and fixed distance between the skin and the distal end of the DBD handpiece. In an embodiment, the SSOE can be topically placed on the interior wall of the cylindrical fitting. The SSOE outgasses oxygen in the area or zone, increasing the oxygen concentration and increasing the ROS and PGS when NTP is created. FIG. 17 shows a cylindrical fitting coupled at the distal end of the DBD handpiece and including SSOE topically placed on an interior wall of the cylindrical fitting, under an embodiment.

Controlling the Atmosphere in the NTP Zone in a DBD Created NTP Device

Figure 18:
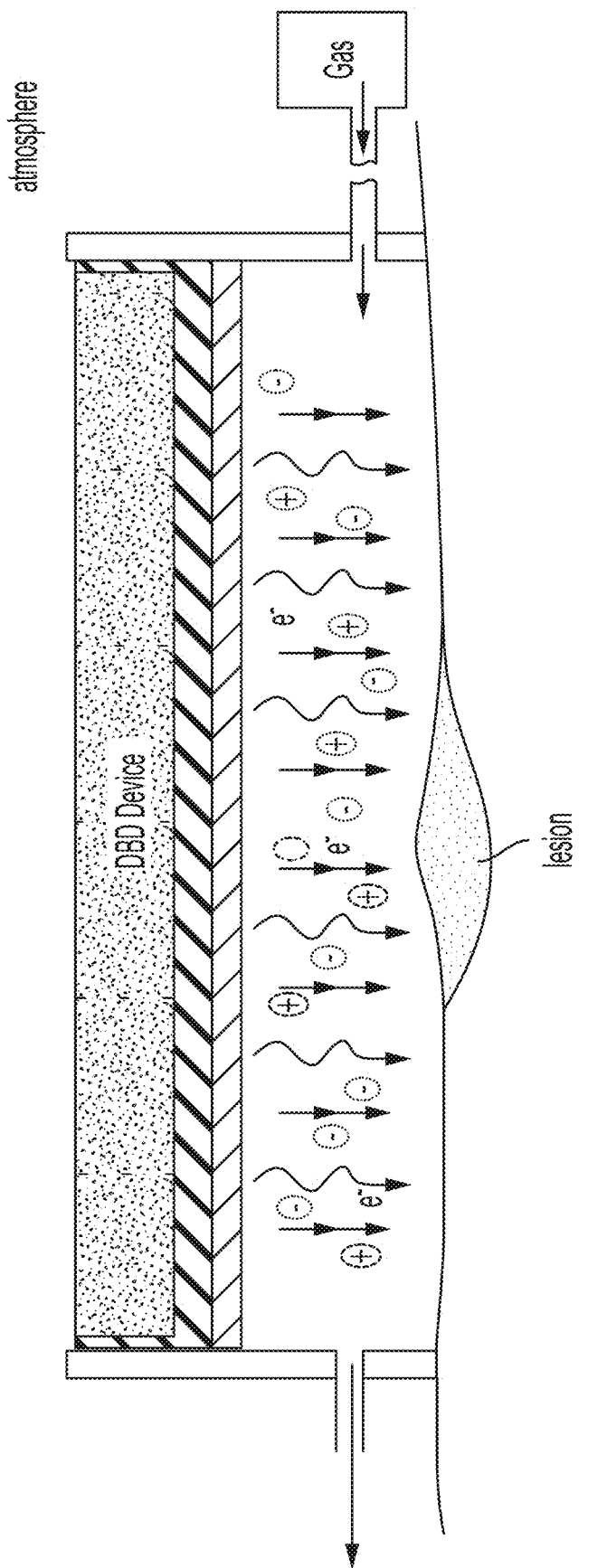
FIG. 18 shows the distal end of the DBD handpiece coupled to a cylindrical fitting including a port configured to couple to a gas supply or source, under an embodiment.

The atmospheric constituents in the volume created between the distal end of a DBD handpiece and the skin can dictate the reactive species and PGS in general. In an embodiment, the cylindrical fitting includes a port configured to couple to a gas supply or source. FIG. 18 shows the distal end of the DBD handpiece coupled to a cylindrical fitting including a port configured to couple to a gas supply or source, under an embodiment. The port is configured to allow gas to flow from a coupled gas source into the volume between the distal end of the DBD handpiece and the skin. The gas can be selected to create the desired PGS, e.g., oxygen, nitrogen, or combination of oxygen and nitrogen.

Indirect Delivery of PGS Using SSGE

The SSGE can be blended with, for example, Ringer's lactate solution (RLS). In one embodiment, RLS is blended into the PFD emulsion, then oxygen is added, resulting in RLS-based SSOE. The RLS-based SSOE can be exposed to the NTP for a period of time, then delivered topically to the target tissue site.

Use of SSOE in Conjunction with Superficial Radiation Therapy

Hyperbaric oxygen (HBO) therapy (HBOT) has been used in conjunction with radiotherapy (RT) and chemotherapy (CT) for the treatment of cancer. HBOT and the systemic delivery of oxygen has been shown to work synergistically with RT and CT in the treatment of cancer.

RT uses the so-called classical oxygen effect in tumor treatment. Upon exposure to radiation, water molecules undergo radiolysis to form unstable hydrogen and hydroxyl radicals. Hydrogen radicals react with molecular oxygen, yielding unstable perhydroxyl radicals and hydrogen peroxide, which cause serious DNA strand damage and consequently lead to cell death. Thus, radiation treatment gives an optimal therapeutic result in well-oxygenated tumor tissue. It was observed that mice breathing pure 1 atm oxygen required a one-third smaller dose of X-rays than mice that were breathing air to achieve similar cancer regression. HBO might play two possible roles when combined with RT, namely it may act as a radiosensitizer, which enhances the effect of radiation, or it may act as a therapeutic agent, reducing delayed radiation injury. A combination of HBO and radiotherapy reduces tumor growth and improves local tumor control, resulting in increased survival time.

Superficial radiation therapy (SRT) is used to treat skin cancers. SRT deliver radiation to the skin. To enhance SRT, SSOE would be applied to the lesion to be treated before treatment. The SSOE is left over the lesion for 1 to 30 minutes, then gently removed or can be left in-place during SRT. The lesion is then subjected to SRT. The SSOE-SRT combination is repeated until SRT is completed. The SSOE can also be used between SRT session and post-SRT to reduce radiation dermatitis and skin side effects of SRT.

It should be observed that the embodiments described in detail herein in accordance with the present invention reside primarily in combinations of method steps and apparatus components related to a cold plasma therapy device used with supersaturated gas emulsion (SSGE). Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A system comprising:
a non-thermal plasma (NTP) device; and
at least one container including supersaturated gas emulsion (SSGE).

2. The system of claim 1, wherein the NTP device comprises at least one of a dielectric barrier discharge device and a jet plasma device.

3. The system of claim 1, wherein the SSGE comprises a dispersed phase of perfluorocarbon (PFC) droplets encapsulated within an aqueous continuous phase.

4. The system of claim 3, wherein the PFC comprises perfluorodecalin (PFD).

5. The system of claim 4, wherein the SSGE comprises at least one of water, humectants, lubricity enhancers, emulsion stabilizers, glycerin, phospholipids, Polawax, vitamin E, and preservative.

6. The system of claim 4, wherein the SSGE includes supersaturated oxygen emulsion (SSOE) comprising PFD and dissolved oxygen, wherein a concentration of the dissolved oxygen is approximately 1.8 milliliters (ml) per gram of SSOE.

7. The system of claim 1, wherein the SSGE is configured to be applied at least one of topically to the treatment site and to a distal region of the NTP device.

8. A method comprising:
configuring a supersaturated gas emulsion (SSGE) for application to a treatment site;
configuring a device to generate a non-thermal plasma (NTP) at the treatment site.

9. The method of claim 8, comprising configuring the SSGE to hydrate tissue of the treatment site.

10. The method of claim 8, comprising configuring the SSGE to increase gas permeability of tissue of the treatment site.

11. The method of claim 8, comprising configuring the SSGE to increase partial pressure of at least one gas in tissue of the treatment site, wherein the at least one gas includes at least one of oxygen and nitrogen.

12. The method of claim 8, comprising configuring the SSGE to increase outgassing and number of select gases at an atmosphere-tissue interface of the treatment site.

13. The method of claim 8, comprising configuring the SSGE to enhance production of plasma generated species during the NTP.

14. The method of claim 8, comprising configuring the SSGE to include a dispersed phase of perfluorocarbon (PFC) droplets encapsulated within an aqueous continuous phase.

15. The method of claim 14, comprising configuring the PFC to include perfluorodecalin (PFD).

16. The method of claim 15, comprising configuring the SSGE to include at least one of water, humectants, lubricity enhancers, emulsion stabilizers, glycerin, phospholipids, Polawax, vitamin E, and preservative.

17. The method of claim 15, comprising configuring the SSGE to include supersaturated oxygen emulsion (SSOE) comprising PFD and dissolved oxygen, wherein a concentration of the dissolved oxygen is approximately 1.8 milliliters (ml) per gram of SSOE.

18. The method of claim 8, wherein the application of the SSGE comprises applying the SSGE to the treatment site topically.

19. The method of claim 8, wherein the application of the SSGE comprises at least one of applying the SSGE to a distal region of a NTP device, and exposing the SSGE to the NTP and subsequently applying the SSGE to the treatment site topically.

20. The method of claim 8, wherein the applying of the NTP comprises use of at least one of a dielectric barrier discharge device and a jet plasma device.

* * * * *